US010430941B2

(12) United States Patent
Buelow et al.

(10) Patent No.: US 10,430,941 B2
(45) Date of Patent: Oct. 1, 2019

(54) IDENTIFYING ABNORMAL TISSUE IN IMAGES OF COMPUTED TOMOGRAPHY

(71) Applicant: KONINKLIJKE PHILIPS N.V., Eindhoven (NL)

(72) Inventors: Thomas Buelow, Grosshansdorf (DE); Rafael Wiemker, Kisdorf (DE); Cristian Lorenz, Hamburg (DE); Steffen Renisch, Hamburg (DE); Thomas Blaffert, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1284 days.

(21) Appl. No.: 14/334,176

(22) Filed: Jul. 17, 2014

(65) Prior Publication Data

US 2014/0330119 A1   Nov. 6, 2014

Related U.S. Application Data

(62) Division of application No. 11/815,973, filed as application No. PCT/IB2006/050362 on Feb. 3, 2006, now Pat. No. 8,892,188.

(30) Foreign Application Priority Data

Feb. 11, 2005 (EP) ..................... 05101024

(51) Int. Cl.
*G06T 7/00* (2017.01)
*A61B 6/00* (2006.01)
(Continued)

(52) U.S. Cl.
CPC .......... *G06T 7/0012* (2013.01); *A61B 6/5217* (2013.01); *G06T 5/50* (2013.01);
(Continued)

(58) Field of Classification Search
None
See application file for complete search history.

(56) References Cited

U.S. PATENT DOCUMENTS

| 5,289,374 A | 2/1994 | Doi et al. |
| 5,365,429 A | 11/1994 | Carmen |

(Continued)

FOREIGN PATENT DOCUMENTS

| JP | 8336524 A | 12/1996 |
| WO | 03070102 A2 | 8/2003 |

OTHER PUBLICATIONS

Li et al. "Selective enhancement filters for nodules, vessels, and airway walls in two- and three-dimensional CT scans." Med. Phys. 30 (8), Aug. 2003. pp. 2040-2051.*

(Continued)

*Primary Examiner* — Angela M Hoffa
(74) *Attorney, Agent, or Firm* — Larry Liberchuk

(57) ABSTRACT

An imaging method for identifying abnormal tissue in the lung is provided, comprising the recording of slice images of the lung by means of X-ray radiation, recording of blood vessels, differentiation of blood vessels and abnormal tissue, segmentation of the abnormal tissue and display of the segmented abnormal tissue on an output device. In addition, a computer tomograph for identifying abnormal tissue in the lung is provided, having a radiation source for recording slice images of the lung and blood vessels by means of X-ray radiation, a computer unit for differentiating the blood vessels from the abnormal tissue and for segmenting the abnormal tissue, as well as an output device for displaying the segmented abnormal tissue. Furthermore, a computer program is provided for controlling a computer tomograph for an identification of abnormal tissue in the lung by means of a radiation source, designed to record slice images of the lung and blood vessels by means of X-ray radiation, to (Continued)

differentiate the blood vessels from abnormal tissue, to segment the abnormal tissue and to control an output device for displaying the abnormal tissue.

11 Claims, 4 Drawing Sheets

(51) Int. Cl.
  *G06T 7/12* (2017.01)
  *G06T 7/149* (2017.01)
  *G06T 5/50* (2006.01)
  *G06T 7/10* (2017.01)
  *A61B 6/03* (2006.01)

(52) U.S. Cl.
  CPC .................. *G06T 7/10* (2017.01); *G06T 7/12* (2017.01); *G06T 7/149* (2017.01); *A61B 6/032* (2013.01); *A61B 6/481* (2013.01); *G06T 2207/10081* (2013.01); *G06T 2207/10116* (2013.01); *G06T 2207/30061* (2013.01); *G06T 2207/30064* (2013.01); *G06T 2207/30101* (2013.01)

(56) References Cited

U.S. PATENT DOCUMENTS

| | | | |
|---|---|---|---|
| 5,627,907 A | 5/1997 | Gur et al. | |
| 5,881,124 A * | 3/1999 | Giger | G06T 7/0012 250/363.04 |
| 6,728,334 B1 | 4/2004 | Zhao | |
| 6,795,521 B2 * | 9/2004 | Hsu | G06T 7/0012 378/4 |
| 6,898,303 B2 * | 5/2005 | Armato, III | G06T 7/0012 378/21 |
| 6,937,776 B2 * | 8/2005 | Li | G06K 9/527 382/131 |
| 7,272,250 B2 | 9/2007 | Schneider et al. | |
| 7,274,810 B2 | 9/2007 | Reeves et al. | |
| 7,315,639 B2 * | 1/2008 | Kuhnigk | G06K 9/34 382/131 |
| 7,397,937 B2 | 7/2008 | Schneider et al. | |
| 7,471,815 B2 | 12/2008 | Hong et al. | |
| 7,492,934 B2 * | 2/2009 | Mundy | A61B 6/032 382/100 |
| 7,583,829 B2 | 9/2009 | Kiraly et al. | |
| 7,783,092 B2 * | 8/2010 | Agam | G06T 7/0012 382/128 |
| 8,059,900 B2 * | 11/2011 | Ferrant | A61B 6/032 382/203 |
| 8,892,188 B2 * | 11/2014 | Buelow | G06T 7/0012 382/131 |
| 9,014,445 B2 * | 4/2015 | Yin | G06T 7/0012 382/128 |
| 9,679,389 B2 * | 6/2017 | Ostrovsky-Berman | G06T 7/11 |
| 9,996,919 B2 * | 6/2018 | Park | A61B 6/032 |
| 2002/0006216 A1 | 1/2002 | Armato, III | |
| 2002/0009215 A1 * | 1/2002 | Armato, III | G06K 9/38 382/131 |
| 2002/0090121 A1 | 7/2002 | Schneider et al. | |
| 2003/0105395 A1 | 6/2003 | Fan et al. | |
| 2003/0167001 A1 | 9/2003 | Allain et al. | |
| 2004/0086161 A1 | 5/2004 | Sivaramakrishna et al. | |
| 2004/0151356 A1 * | 8/2004 | Li | G06K 9/527 382/131 |
| 2004/0252870 A1 | 12/2004 | Reeves et al. | |
| 2004/0267114 A1 * | 12/2004 | Mundy | A61B 6/032 600/427 |
| 2005/0207630 A1 | 9/2005 | Chan et al. | |
| 2005/0244042 A1 * | 11/2005 | Sirohey | G06T 7/0012 382/131 |
| 2005/0259854 A1 * | 11/2005 | Arimura | G06T 7/0012 382/130 |
| 2006/0079743 A1 * | 4/2006 | Ferrant | A61B 6/032 600/407 |
| 2009/0005693 A1 * | 1/2009 | Brauner | A61B 6/508 600/481 |
| 2009/0123053 A1 * | 5/2009 | Mundy | A61B 6/032 382/132 |
| 2015/0139525 A1 * | 5/2015 | Mundy | A61B 6/032 382/132 |

OTHER PUBLICATIONS

Bartz et al: "Hybrid Segmenation and Exploration of the Human Lungs"; 2003, IEEE Visualization, pp. 177-1874.
Bulow et al: "A Method for Lung Nodule Visualization From Multi-Slice CT Data": 2005, International Congress Series, vol. 1281, pp. 1127-1131.
Deschamps et al: "Fast Extraction of Tubular and Tree 3D Surfaces With Front Propagation Methods"; 2002, Proc. 16th Conf. on Pattern Recognition, vol. 1., pp. 731-734.
GE Healthcare: CT Application Option:Lung Analysys; Nov. 29, 2004, http:/www.gemedicalsystemseurope.com/euen/rad/ct/applications/ling-analysis.html.
Goo et al: "Automated Lung Nodule Detection at Low-Dose CT:Preliminary Experience"; 2003, Korean Journal of Radiology, 4(4), pp. 211-216.
Kawata et al: Pulmonary Nodule Segmentation in Thoracic 3-D CT Images Integrating and Boundary Region Information, 2003, Proc. of SPIE, vol. 5032, pp. 1520-1530.
Schlatholter et al: Simultaneous Segmentation and Tree Reconstruction of the Airways for Virtual Bronchoscopy, 2002, Proc. of SPIE, vol. 4684, pp. 103-113.
Zhao et al: "Automatic Detection of Small Lung Nodules on CT Utilizing a Local Density Maximum Algorithm"; 2003, J. of Applied Clinical Medical Physics, vol. 4, Issue 3, pp. 248-260.
Kirbas et al: "Vessel Extraction Techniques and Algorithms: A Survey"; IEEE Proc. Symp. on Bioinformatics and Engineering, 2003, pp. 238-245.
Bulow et al:"A General Framework for Tree Segmentation and Reconstruction From Medical Volume Data"; MICCAI LNCS, 2004, vol. 3216, pp. 533-540.
Frangi et al: "Multiscale Vessel Enhancement Filtering"; MICCAI, 1998, pp. 130-137.
Lorenz et al: "Simultaneous Segmentation and Tree Reconstruction of the Coronary Arteries in MSCT Images"; Proc. of SPIE, 2003, vol. 5031, pp. 167-177.
Lorenz et al: A Multi-Scale Line Filter With Automatic Scale Selection Based on the Hession Matrix Medical Image Segmentation; Scale-Space LNCS, 1997, vol. 1252, pp. 152-163.

* cited by examiner

IDENTIFYING ABNORMAL TISSUE IN IMAGES OF COMPUTED TOMOGRAPHY

CROSS REFERENCE TO RELATED APPLICATIONS

This application is a divisional of U.S. application Ser. No. 11/815,973 filed Aug. 10, 2007, which is a national filing of international application serial number PCT/IB2006/050362, filed Feb. 3, 2006, which claims the benefit of EP application serial number 05101024.7 filed Feb. 11, 2005, all of which are incorporated herein by reference.

FIELD OF THE INVENTION

The invention relates to an imaging method for computed, to a computer tomograph and to a computer program.

BACKGROUND OF THE INVENTION

In the technical field of medical radiology, computer tomographs have gained increasingly in importance in recent years. In computed tomography, x-ray radiation is irradiated from a radiation source towards an object to be examined, as a rule a patient, and, on the basis of the attenuation of the X-ray radiation after this has passed through the object to be examined, an image is produced on a monitor. In this process, the radiation source is moved around the object to be examined and from different positions records images of individual slices of the object to be examined. The individual slice images or tomograms can finally be added together and produce a three-dimensional image on the monitor of the object to be examined. Specifically in the case of computed tomography recordings of the lung, the objective is the identification of abnormal tissue, known as nodules, in the lung at an early stage. In order to prepare an analyzable image of the lung, other structures apart from the lung, for instance the thoracic cage or the heart, are suppressed in the slice images. This is achieved by essentially known segmentation methods, in which slice images of structures of the object to be examined are subtracted from one another and individual structures are thereby removed from the resulting image. When two slice images, which approximately congruently show a structure to be removed, are arranged one on top of the other and the gray-scale values of the slice images are subtracted from each other, the image of the structure is removed from the two slice images. In a special process, interfering structures are removed from the image, so that only the lung cavity and the blood vessels appear. The blood vessels are in this case rendered recognizable in the X-ray image essentially by means of a contrast medium injected into the patient and in terms of contrast with respect to the background, here the lung cavity, stand out clearly. The problem with this process, however, is that the contrast between abnormal tissue and the blood vessels containing the contrast medium is low, the attenuation values, also known as Hounsfield values, received by the detector device of the computer tomograph do not differ significantly from one another. In particular, abnormal tissue that lies close to or on the blood vessels is not identified in the images owing to the similar gray-scale values of the abnormal tissue and the blood vessels.

SUMMARY OF THE INVENTION

It is an object of the present invention to render abnormal tissue in the lung clearly identifiable by means of computed tomography.

That object is achieved by the invention by means of the features disclosed herein.

In accordance with the invention, an imaging method for identifying abnormal tissue in the lung is provided, comprising the recording of slice images of the lung by means of X-ray radiation, recording of blood vessels, differentiation of blood vessels and abnormal tissue, segmentation of the abnormal tissue and display of the segmented abnormal tissue on an output device. Furthermore, a computer tomograph for identifying abnormal tissue in the lung is provided, having a radiation source for recording slice images of the lung and blood vessels by means of X-ray radiation, a computer unit for differentiating the blood vessels from abnormal tissue and for segmenting the abnormal tissue, as well as an output device for displaying the segmented abnormal tissue. In addition, a computer program for controlling a computer tomograph for identifying abnormal tissue in the lung and having a radiation source for recording slice images of the lung and of blood vessels by means of X-ray radiation is provided, for differentiating the blood vessels from abnormal tissue, for segmenting the abnormal tissue and for controlling an output device for displaying the abnormal tissue. By means of the invention, abnormal tissue in the vicinity of blood vessels is distinguishable from these. This appreciably simplifies the subsequent analysis of the results of the imaging method.

Advantageous embodiments of the invention are specified in the independent claims.

In one embodiment of the invention, an imaging method for identifying abnormal tissue in the lung in provided, comprising the recording of slice images of the lung by means of X-ray radiation, recording of blood vessels and differentiation of blood vessels and abnormal tissue by evaluation of the diameter of the blood vessels and of the abnormal tissue at different locations, and display of the abnormal tissue on an output device. Together with this a suitable distinguishing criterion is used, in order to single out the blood vessels interfering with identification of the abnormal tissue and consequently to be able to display exclusively the abnormal tissue.

In another embodiment, a computer tomograph is provided for identifying abnormal tissue in the lung using a radiation source for recording slice images of the lung and of blood vessels by means of X-ray radiation, having a computer unit for differentiating blood vessels and abnormal tissue by evaluation of the diameter of the blood vessels and of the abnormal tissue at different locations, as well as an output device for display of the abnormal tissue.

In addition, in a further embodiment, a computer program for controlling a computer tomograph for identifying abnormal tissue in the lung using a radiation source is provided, designed for recording slice images of the lung and of blood vessels by means of X-ray radiation, for operation of a computer unit of the computer tomograph for differentiating blood vessels and abnormal tissue by evaluation of the diameter of the blood vessels and of the abnormal tissue at different locations, and for controlling an output device for display of the abnormal tissue.

To determine the diameter of the blood vessels and of the abnormal tissue in the slice images for the purpose of differentiating these from one another, in one embodiment starting points in the blood vessels can be calculated and, commencing from the starting points, a wave front of constant speed is generated, which is halted at the boundaries of the blood vessels. By means of the wave fronts, which propagate in the blood vessels and in the abnormal tissue and terminate at the boundaries thereof, which is detectable by means of the contrast in the gray-scale values at the boundary between the blood vessels and the abnormal tissue on the one hand and the surroundings thereof on the other hand, the diameter of the blood vessels and of the abnormal tissue is determinable in an exemplary manner in the image produced.

These and other aspects of the invention are apparent from and will be elucidated, by way of non-limitative example, with reference to the embodiments described hereinafter.

DETAILED DESCRIPTION OF EMBODIMENTS

Figure 1:
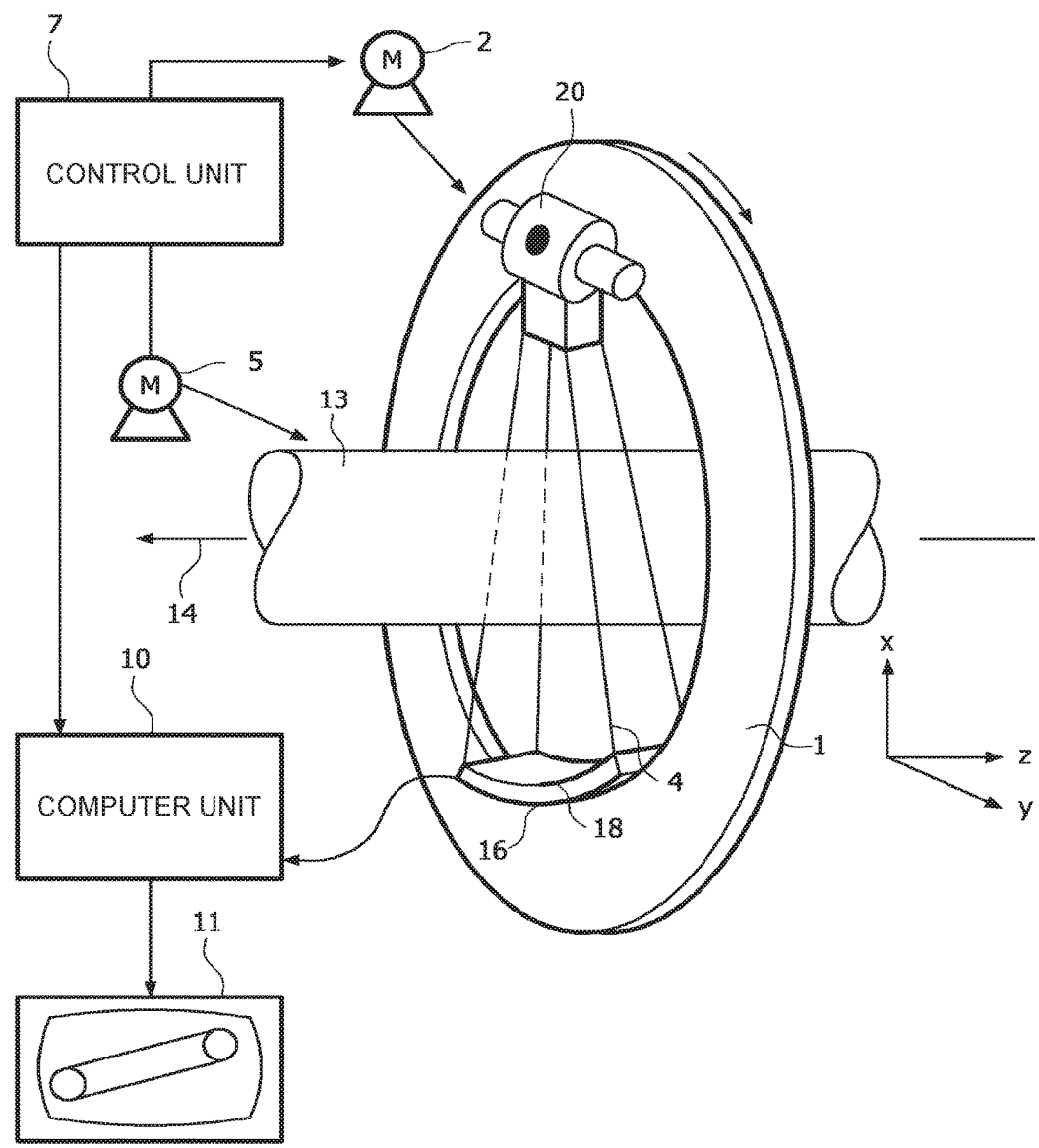
FIG. 1 shows a schematic view of part of a computer tomograph.

FIG. 1 shows a schematic view of a support or a gantry 1, which is able to rotate along the circular path marked by the curved arrow parallel to the y-plane of the coordinate system illustrated. For that purpose, the gantry 1 is driven by a motor 2 at a preferably constant but adjustable angular velocity. A radiation source 20, for example an X-ray tube, is fixed to the gantry 1, and includes a collimator arrangement, which extracts a fan-shaped beam bundle 4 from the radiation produced by the radiation source 20. The beam bundle 4 is illustrated schematically by means of two lines, which bound the beam bundle 4. The fan-shaped beam bundle 4 penetrates at least partially through an object 13, which in FIG. 1 is shown as a portion of a cylinder; the object 13 is usually a patient or part of a patient on a patient support table and in this case the object comprises a lung or portions thereof, the lung cavity 5, which comprises the lung, pulmonary tissue and blood vessels 6, which permeate the pulmonary tissue. After the rays of the radiation source 20 have passed through the object 13, the beam bundle 4 is incident on a detector device 16 connected to the gantry 1 on a side opposite to the radiation source 20 and having a detector surface 18, which comprises a plurality of detector elements, which in this embodiment are arranged in rows. As the gantry 1 moves, the radiation source 20 and the detector device 16 move correspondingly. Each detector element of the detector device 16 on which a beam of the beam bundle 4 is incident delivers a measured value for the different positions of the moving radiation source 20, and this measured value can be used for the imaging.

The object 13 is displaced on a patient support table by a motor 5, parallel to the axis of rotation 14 of the gantry 1 in the direction of the z-axis. Alternatively and equivalently, the gantry 1 could be displaced in that direction.

If the motors 2 and 5 run simultaneously, the radiation source 20 and the detector unit 16 describe a spiral or helical trajectory or detector path around the object 13.

The measured values acquired by the detector unit 16 are fed to a computer unit 10 of the computer tomograph, which is connected to the detector unit 16, for example, via a contactlessly operating data transmission. The computer unit 10 calculates measured values, reconstructs the distribution of the absorption of the radiation of the radiation source 20 caused substantially by the object 13 and displays it on an output device 11, generally speaking a monitor. The two motors 2, 5, the computer unit 10, the radiation source 20 and the transfer of the measured values from the detector unit 16 to the computer unit 10 are controlled by a control unit 7. The control unit 7 and the computer unit 10 can form one unit; in particular, a computer program for controlling the computer tomograph can be filed in a memory of the control unit 7 or in the computer unit 10.

The computer tomograph records slice images of the lung as follows: the radiation source 20 irradiates slices of the lung whilst the lung is as immobile as possible and the movement of the object 13 in the direction of the z-axis is at rest. After recording a tomogram, the patient and the lung are displaced in the direction of the z-axis, the object 13 is halted again and an adjacent slice of the lung is recorded. This is also known as step-and-shoot. Further, the computer tomograph can also be designed so that the object 13 moves in the direction of the z-axis during recording, so that a helical or spiral path or trajectory of the radiation source 20 around the object 13 is achieved.

Figure 2:
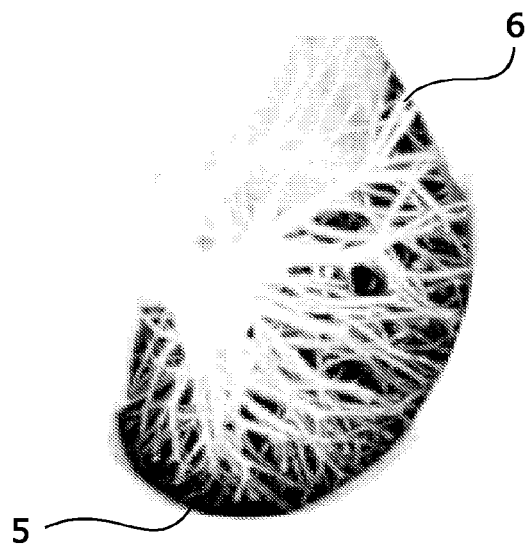
FIG. 2 shows a three-dimensional image recording of a lobe of the lung with blood vessels and the lung cavity.

FIG. 2 shows a three-dimensional view of a portion of a lung, which is encompassed by the object 13, with the lung cavity 5 and blood vessels 6, which form a kind of vascular tree with branchings of the blood vessels 6. The term lung cavity 5 here denotes the space of the lung filled by pulmonary tissue. The blood vessels 6 permeate the space and the pulmonary tissue in the lung cavity 5. The three-dimensional image according to FIG. 2 is made up of a plurality of superimposed slice images that have been recorded as described above. The presentation is also known as a maximum intensity projection. After recording the tomograms, interfering structures of the body are segmented, for instance, the heart or the thoracic cage, that is, these are removed from the image. In the image processing, the blood vessels 6 and the lung cavity 5 are separated from their surroundings, the term surroundings in this case including all structures of the body that are detected by the described imaging method. After segmentation of the structures of the body, the lung cavity 5 and the blood vessels 6 are left, as illustrated.

Figure 3:
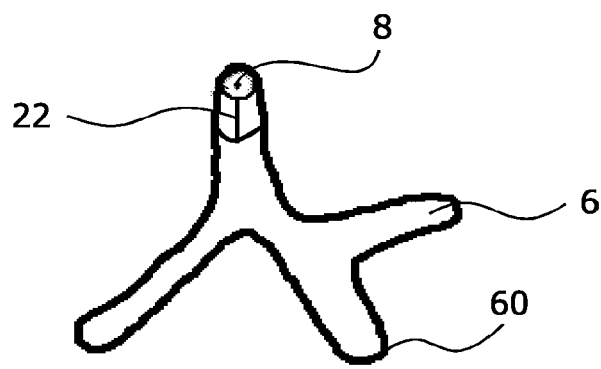
FIG. 3 shows a schematic view of blood vessels, which are traversed, starting from an initial point, by a wave front.

FIG. 3 shows a schematic view of blood vessels 6 as shown in FIG. 2 with several branchings. At one end of the blood vessels 6 an initial point 8 has been entered, which is used as the starting point for a wave front 22 that propagates in the blood vessels 6. The location at which the initial point 8 lies can be determined by the user in the image of the blood vessels 6 portrayed on the output device 11 or can be determined by image-processing software in the computer unit 10 of the computer tomograph. A model of blood vessels 6 is portrayed, which are recorded as the image and segmented from their surroundings. The thick-walled limit or boundary 60 of the blood vessels 6 marks the transition of the difference in contrast against the surroundings of the blood vessels 6 in the image. The wave front 22 commences at a boundary 60 of the blood vessels 6 at one side of the blood vessels 6 and terminates at the boundary 60 on an opposite side of the blood vessels 6. The gray-scale values of the image data sets on which the images are based deliver contrast values for identifying the boundary 60 of the blood vessels 6 to the computer unit 10. The contrast between the surroundings of the blood vessels 6 and the blood vessels 6 is high, so the blood vessels 6 can therefore be clearly differentiated from their surroundings. The wave front 22 moves along only within the images of the blood vessels 6; when a contrast threshold at the boundary 60 of the blood vessels 6 is detected, the wave front 22 terminates at this location. In FIG. 3, a line has been drawn from the initial point 8 to the wave front 22, which shows the distance the wave front 22 has already propagated in the image of the blood vessels 6. The distance between the start and the end of the wave front 22 at opposite boundaries 60 of the blood vessels 6 is detected by the computer unit 10. This is approximately the same as the diameter of the blood vessel 6. If the distance thus measured lies in a specific value range, then it is concluded therefrom that the wave front 22 is propagating in a blood vessel 6, as illustrated in FIG. 3. For that purpose, the distances measured, which correspond approximately to the diameter of the blood vessels 6, are compared in the computer unit 10 with comparison values.

Figure 4:
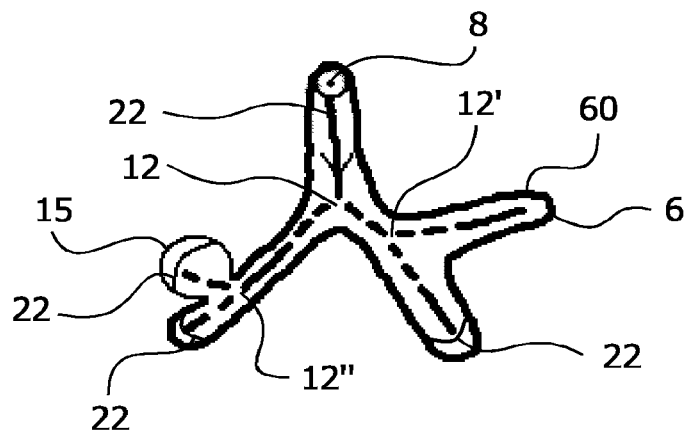
FIG. 4 shows a schematic view of the blood vessels as shown in FIG. 3 with abnormal tissue.

FIG. 4 shows a similar view to FIG. 3, in which the wave front 22 has progressed as far as the end of the blood vessels 6. At junctions of the blood vessels 6, where the blood vessels 6 divide up into several branches, there are branching points 12, 12', 12" at which the wave front divides, so that independent wave fronts 22 develop, which propagate into the respective branches of the blood vessels 6. At the first branching point 12, the wave front 22 divides into two branches of the blood vessels, two wave fronts 22 developing. At the second branching point 12', the wave front 22 that developed at the first branching point 12 divides into two wave fronts 22, which each propagate in a respective branch of the blood vessels 6 as far as the end of the branches of the blood vessels 6, and this is detected by the difference in contrast compared with the surroundings of the blood vessels 6. The difference in contrast between the blood vessels 6 and the surroundings of the blood vessels 6 is great, and therefore easily detectable. Behind the branching points 12, 12', 12", the lines that indicate the propagation path of the wave front 22 are drawn as broken lines. From the first branching point 12, viewed in the direction of the wave front 22, a new wave front branches off, and divides again at the branching point 12". At the branching point 12", the blood vessels 6 do not branch, on the contrary, abnormal tissue 15 adjoins the blood vessels 6. The abnormal tissue 15 is a pulmonary nodule, which is shown here as being approximately circular. Behind the branching point 12", in the direction of the arrow that indicates the propagation direction of the wave front 22, the wave front 22 propagates into a branch of the blood vessels 6 and into the abnormal tissue 15. As mentioned, at different locations in the blood vessels 6 the distance at the wave front 22 from a boundary 60 of the blood vessel 6 to the opposite boundary 60 is determined continuously, this distance being approximately the same as the diameter of the blood vessels 6, in the case of the abnormal tissue 15 approximately the same as the diameter of this at different locations. Behind the second branching point 12", in the vicinity of the blood vessels 6 additionally a distance that corresponds approximately to the customary diameter of the blood vessels 6 is determined. In the computer unit 10 of the computer tomograph, by means of a comparison it is inferred from the determined distance that a blood vessel 6 is present. In the vicinity of the abnormal tissue 15, however, a distance between the opposite ends of the wave front 22, which lie between the boundaries 60 of the abnormal tissue 15, is determined, this distance differing from the diameter of the blood vessels 6, in this case being larger. From this different measured diameter in the pulmonary nodule compared with the diameter of the blood vessels 6, the presence of abnormal tissue 15 is inferred. The diameter at the wave front 22 under consideration is compared in particular with measurements close in time, since the diameter of the blood vessels 6 does vary too. A further criterion for determining the abnormal tissue 15 in the computer unit 10 is that the wave front 22 is not able to propagate far in the region of the pulmonary nodule, but after few measurements, after a short run, comes up against the boundaries 60 vis-à-vis the surroundings, which is detected. A further criterion for determining the abnormal tissue 15 in the computer unit 10 is that the measured diameter of the abnormal tissue 15 changes markedly. On the basis of the circular or oval form of pulmonary nodules, upon a change in the diameter at the wave front 22 such that first of all an enlargement to the maximum diameter and thereafter a decrease in diameter in conformity with the circular form occurs, the presence of abnormal tissue 15 can be inferred. If one or more of the above three criteria are present, abnormal tissue 15 is assumed to exist on the blood vessels 6. The regions of the image at which this is detected are removed from the rest of the image, the image of the blood vessels 6, so that image data only of the abnormal tissue 15 is present. This is achieved by segmenting the image data of the blood vessels 6 with abnormal tissue 15 from the image data of the blood vessels 6 with no abnormal tissue 15. Thereafter a display on the output device 11 of the abnormal tissue 15 without interfering superimposed influences caused by the blood vessels 6 can be put to use.

Figure 5:
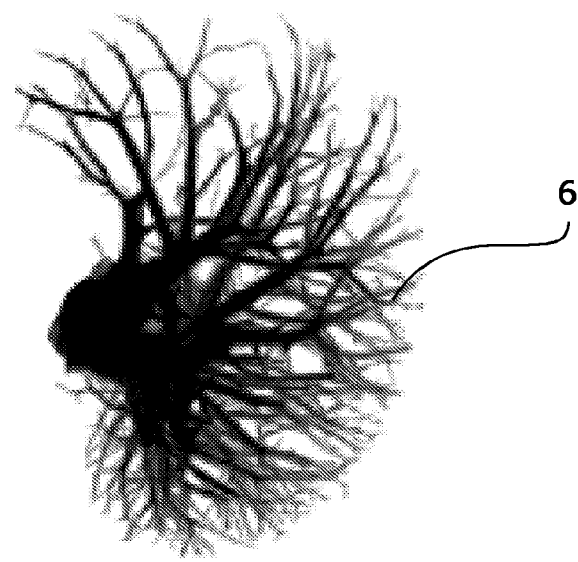
FIG. 5 shows a three-dimensional image recording of the blood vessels segmented from their surroundings.

FIG. 5 shows a three-dimensional view of blood vessels 6 that are segmented from their surroundings, the structures or body parts in the body of the patient. The view is also known as a maximum intensity projection. The tree structure of the blood vessels 6 having a plurality of branchings, at which the blood vessels 6 divide, can be seen. The three-dimensional view is prepared by arranging the slice images generated in succession by the computer tomograph, the display in three spatial planes being generated on the output device 11 by superimposing the slice images. In this segmented view, in the individual slice images or the superimposed tomograms, as in FIG. 5, no abnormal tissue 15 is present. This recording of the blood vessels 6, also called a vascular tree, is removed in one step from the corresponding recording of the lung cavity 5 with blood vessels 6 and abnormal tissue 15, so that a recording of the lung cavity 5 with abnormal tissue 15 is created. In the last-mentioned recording, the abnormal tissue 15 is easily visible in the lung cavity 5.

Figure 6:
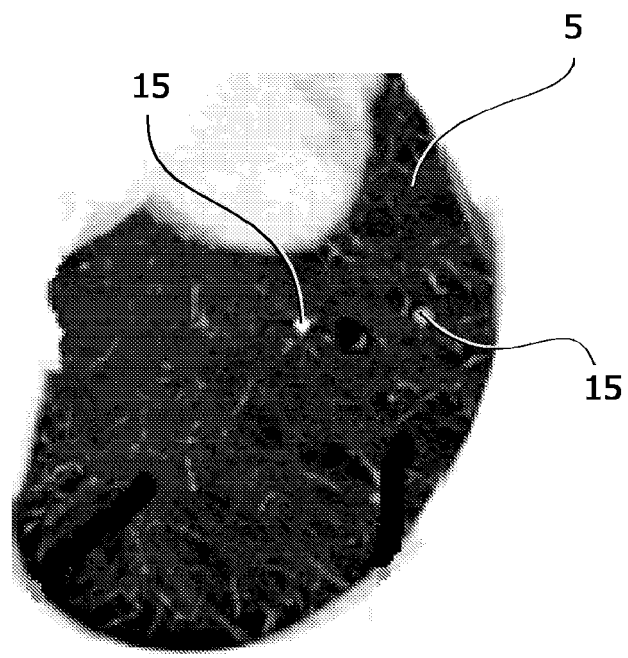
FIG. 6 shows a slice image of the lung cavity, segmented from its surroundings, with abnormal tissue.

FIG. 6 shows a three-dimensional view of the lung cavity 5, in which the blood vessels 6 have been removed by the imaging method of segmentation. The view is also known as a maximum intensity projection. Similar to the view as shown in FIG. 5, a plurality of slice images of the lung cavity 5, here several hundred slice images, are arranged one upon the other, so that a spatial arrangement in three planes is produced. The vascular tree, which comprises the blood vessels 6, is removed from the image data of the computer unit 10, as described above. The abnormal tissue 15 is differentiated from the blood vessels 6 as described above. The abnormal tissue 15 is thus segmented or isolated, that is, shown separately from some or all structures in its surroundings, for instance other organs, the blood vessels 6 of the lung. By subtracting the individual slice images that combine to form the three-dimensional view, with and without differentiation of the blood vessels 6 from the abnormal tissue 15, the view shown in FIG. 6 is produced, in which only image regions that are detected as abnormal tissue 15 are observable. Clearly visible in FIG. 6 are two pulmonary nodules of the abnormal tissue 15, which stand out as light-colored areas against the remaining lung cavity 5. The view as shown in FIG. 6 can be displayed on the output device 11 to a user, who, from the recording, accesses a specific section of the recording by means of an input device, for instance a computer mouse, for input into the computer unit 10 of the computer tomograph. The accessed section in FIG. 6 comprises as a rule the light-colored abnormal tissue 15. After the user has selected the section, in the computer unit 10 of the computer tomograph it is determined in which slice image of the plurality of added slice images as per FIG. 6 the abnormal tissue 15 is substantially displayed. A slice image that shows the abnormal tissue 15 is selected, no further consideration is then paid to the remaining slice images that do not show the abnormal tissue 15. The selected individual slice image that substantially shows the abnormal tissue 15 is subsequently displayed on the output device 11. In this manner, interfering influences of other slice images are excluded. The position of the abnormal tissue 15 in the pulmonary tissue is also determinable in a perpendicular direction into the image plane, since with knowledge of the individual slice image also the position in this direction is established. The individual slice images are recorded starting from a first slice image at the start of the lung cavity 5 to a final slice image at the opposite end of the lung cavity 5 and have a specific number and thickness. With knowledge of the number and thickness of the slice images, and of the distance between the first and last slice image, the position of the selected slice image perpendicularly in the image plane as shown in FIG. 6 is determinable. Since this slice image reproduces the abnormal tissue 15, the corresponding position of the abnormal tissue 15 is, as it were, known. This determination of the position is vital for the medical treatment.

Figure 7:
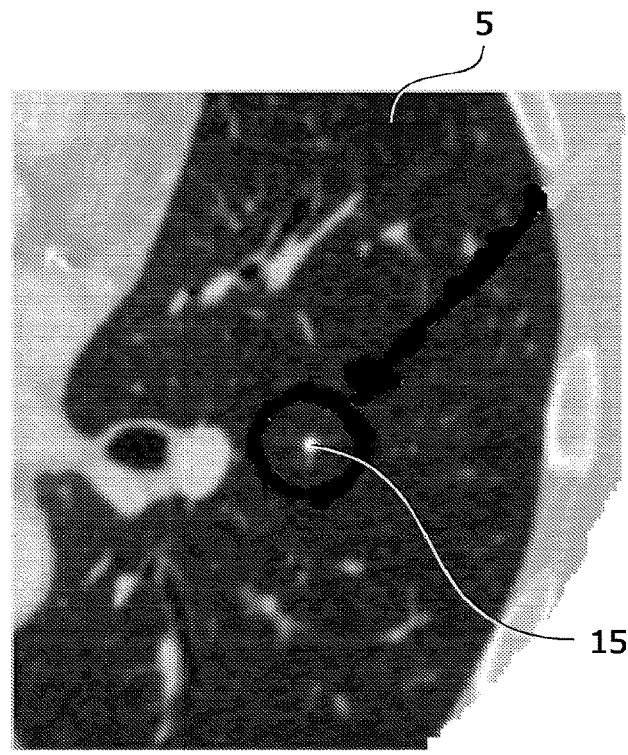
FIG. 7 shows a slice image of the lung cavity, segmented from its surroundings, with blood vessels and abnormal tissue.
Figure 8:
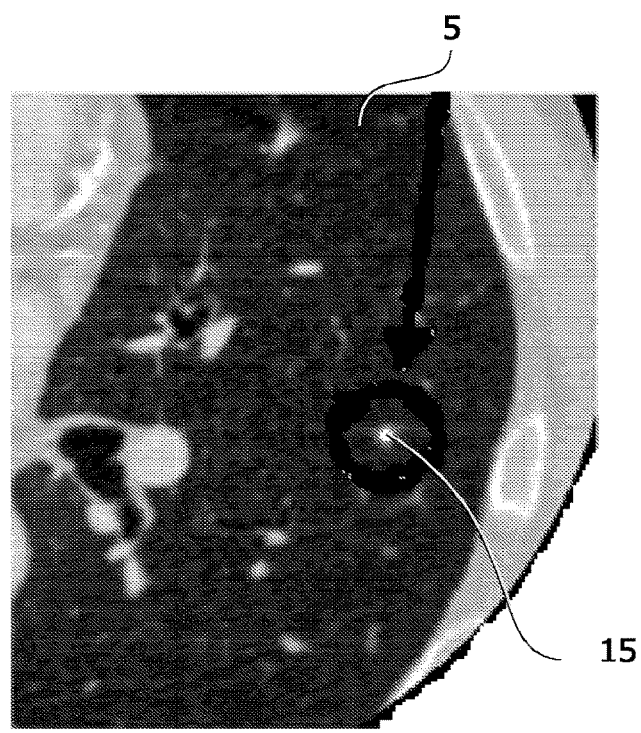
FIG. 8 shows a further slice image of the lung cavity, segmented from its surroundings, with abnormal tissue.

FIG. 7 shows a view of the lung cavity 5, similar to FIG. 6, in which in contrast thereto no slice images are arranged one upon the other; rather, an individual slice image from the composite three-dimensional view according to FIG. 6 is shown, similar to the above-described individual slice image which is selected. Unlike the view shown in FIG. 6, here the blood vessels 6 are present in the image, visible as light-colored streaks in the slice image, a segmentation of the lung cavity 5 from the blood vessels 6 has not been carried out. An approximately circular patch is observable in the image, which originates from the same abnormal tissue 15 as the left of the two circular patches shown in FIG. 6. FIG. 8 shows a slice image similar to FIG. 7, without segmentation of the blood vessels 6, which is likewise a slice image put together to form the three-dimensional image shown in FIG. 6. Here, an approximately circular, light-colored patch is observable, which originates from the same abnormal tissue 15 as the right of the two circular patches shown in FIG. 6. From FIGS. 7 and 8 it is observable that abnormal tissue 15 in this case is discernible even by means of individual slice images, and the detection of abnormal tissue 15 even without segmentation of the blood vessels 6 becomes possible.

As an alternative possibility of differentiating the blood vessels 6 from the abnormal tissue 15, the computer unit 10 is designed to differentiate the gray-scale values of the blood vessels 6 from the gray-scale values of the abnormal tissue 15 by means of the eigenvalues of a Hessian matrix. In this case, the gray-scale structure of the recordings is analyzed in the computer unit 10. If a high gray-scale value is present at a location of the recordings, then the computer unit 10 recognizes the existence of a blood vessel 6 at this location, if a low gray-scale value is present at a location of the recordings, then the computer unit 10 recognizes the existence of abnormal tissue 15 at this location. Reference is made to the publications of C. Lorenz, I.-C. Carlsen, T. M. Buzug, C. Fassnacht and J. Weese, entitled "A Multi-Scale Line Filter with Automatic Scale Selection based on the Hessian Matrix for Medical Image Segmentation", Scale-Space, 1997, LNCS 1252, pages 152-163 and A. F. Frangi, W. J. Niessen, K. L. Vincken, M. A. Viergever, entitled "Multiscale Vessel Enhancement Filtering", MICCAI, 1998, pages 130-137, which are incorporated in the description by reference.

The invention claimed is:

1. A method, comprising
recording slice images of a lung through X-ray radiation to produce slice images of the lung, each slice image corresponds to a different position of the lung, where at least one slice image of the slice images includes lung cavity, blood vessels and an abnormal tissue, wherein the lung cavity, the blood vessels and the abnormal tissue are represented through gray-scale values;
segmenting the blood vessels in the slice images of the lung, wherein the gray-scale values of the blood vessels are differentiated from the gray-scale values of the abnormal tissue through eigenvalues of a Hessian matrix;
removing the segmented blood vessels from the slice images of the lung; and
displaying at least one of the slice images of the lung with the removed segmented blood vessels on an output device.

2. The method of claim 1, wherein displaying the at least one of the slice images of the lung with the removed segmented blood vessels comprises:
displaying a maximum intensity projection image formed from the slice images with the segmented blood vessels removed.

3. The method of claim 1, wherein
the least one slice image includes the lung cavity and the abnormal tissue.

4. The method of claim 1, wherein
boundaries of the blood vessels are detected with a multi-scale line filter and the Hessian matrix.

5. The method of claim 1, wherein boundaries of the blood vessels are detected with a multi-scale vessel enhancement filter and the Hessian matrix.

6. A computer tomograph, comprising:
a radiation source configured to record slice images through X-ray radiation, each slice image corresponds to a different position of the lung, where at least of slice image of the slice images include lung cavity, blood vessels and an abnormal tissue, wherein the lung cavity, the blood vessels and the abnormal tissue are represented through gray-scale values; and
a computer unit configured to:
segment the blood vessels in the slice images of the lung, wherein the gray-scale values of the blood vessels from the gray-scale values of the abnormal tissue through eigenvalues of a Hessian matrix;
remove the segmented blood vessels from the slice images of the lung; and
display at least one slice image with the segmented blood vessels removed on an output device.

7. The computer tomograph of claim 6, wherein the displayed at least one slice image with the segmented blood vessels removed comprises a maximum intensity projection image formed from the slice images with the segmented blood vessels removed.

8. The computer tomograph of claim 6, wherein the at least one slice image with the segmented blood vessels removed includes the lung cavity and the abnormal tissue.

9. The computer tomograph of claim 6, wherein boundaries of the blood vessels are detected with a multi-scale line filter and the Hessian matrix.

10. The computer tomograph of claim 6, wherein boundaries of the blood vessels are detected with a multi-scale vessel enhancement filter and the Hessian matrix.

11. A non-transitory computer readable storage medium encoded with computer readable instructions, which, when executed cause a processor to:
  record at least one slice image of a lung through X-ray radiation to produce a slice image of the lung, where the slice image of the lung includes lung cavity, blood vessels and an abnormal tissue represented through gray-scale values;
  segment the blood vessels in the at least one slice image by differentiating the gray-scale values of the blood vessels from the gray-scale values of the abnormal tissue through eigenvalues of a Hessian matrix;
  remove the segmented blood vessels from the at least one slice image of the lung leaving the lung cavity and the abnormal tissue; and
  display the at least one slice image with the segmented blood vessels removed on an output device leaving the lung cavity and the abnormal tissue.

* * * * *